United States Patent
Cocco et al.

(10) Patent No.: US 10,074,178 B2
(45) Date of Patent: Sep. 11, 2018

(54) INTRA-ORAL IMAGE ACQUISITION ALIGNMENT

(71) Applicant: Dental Imaging Technologies Corporation, Hatfield, PA (US)

(72) Inventors: George John Cocco, Havertown, PA (US); Adam T. Palermo, Philadelphia, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 520 days.

(21) Appl. No.: 14/610,184

(22) Filed: Jan. 30, 2015

(65) Prior Publication Data
US 2016/0225151 A1 Aug. 4, 2016

(51) Int. Cl.
*G06T 7/00* (2017.01)
*A61B 6/14* (2006.01)
(Continued)

(52) U.S. Cl.
CPC .......... *G06T 7/0028* (2013.01); *A61B 5/0088* (2013.01); *A61B 6/145* (2013.01);
(Continued)

(58) Field of Classification Search
CPC .......... G06T 7/0028; G06T 7/90; G06T 7/33; G06T 7/13; G06T 7/0012; G06T 2207/30036; H04N 5/23293; H04N 7/18; H04N 5/33; G06K 9/4652; G06K 9/4604; G06K 2009/4666; G06F 17/3028;
(Continued)

(56) References Cited

U.S. PATENT DOCUMENTS 4,409,616 A 10/1983 Ledley
6,276,934 B1 * 8/2001 Rakocz ................ A61B 1/0669
433/29
(Continued)

FOREIGN PATENT DOCUMENTS

WO 2006092800 A2 9/2006
WO 2008033218 A1 3/2008
(Continued)

OTHER PUBLICATIONS

Extended European Search Report from the European Patent Office for Application No. 16153430.0 dated Jun. 29, 2016 (8 pages).

*Primary Examiner* — Sath V Perungavoor
*Assistant Examiner* — Philip Dang
(74) *Attorney, Agent, or Firm* — Michael Best & Friedrich LLP

(57) ABSTRACT

Systems and methods are presented for assisting in providing consistent alignment of a handheld intra-oral imaging device for a series of images. Live image data of the patient is received from the intra-oral image capture device and displayed on the display. A previously stored intra-oral image of the patient is accessed from the non-transitory memory and an alignment mask is generated based on the accessed previously stored intra-oral image. The alignment mask is displayed on the display overlaid onto the live image data. The system captures a new intra-oral image of the patient from the live image data and stores the new intra-oral image to the non-transitory memory.

34 Claims, 11 Drawing Sheets

(51) Int. Cl.
*A61B 6/00* (2006.01)
*A61B 5/00* (2006.01)
*G06F 17/30* (2006.01)
*G06K 9/46* (2006.01)
*G06K 9/62* (2006.01)
*H04N 5/232* (2006.01)
*H04N 5/33* (2006.01)
*H04N 7/18* (2006.01)
*G06T 7/33* (2017.01)
*G06T 7/13* (2017.01)
*G06T 7/90* (2017.01)

(52) U.S. Cl.
CPC ............ *A61B 6/463* (2013.01); *A61B 6/5235* (2013.01); *G06F 17/3028* (2013.01); *G06K 9/4604* (2013.01); *G06K 9/4652* (2013.01); *G06K 9/6201* (2013.01); *G06T 7/0012* (2013.01); *G06T 7/13* (2017.01); *G06T 7/33* (2017.01); *G06T 7/90* (2017.01); *H04N 5/23293* (2013.01); *H04N 5/33* (2013.01); *H04N 7/18* (2013.01); *G06K 2009/4666* (2013.01); *G06T 2207/30036* (2013.01)

(58) Field of Classification Search
CPC ..... A61B 5/0088; A61B 6/145; A61B 6/5235; A61B 6/463
See application file for complete search history.

(56) References Cited

U.S. PATENT DOCUMENTS

| | | | | |
|---|---|---|---|---|
| 7,057,639 | B2* | 6/2006 | Spoonhower | A61B 1/00016 348/65 |
| 7,193,219 | B2* | 3/2007 | Schick | A61B 5/0088 250/370.09 |
| 7,376,279 | B2* | 5/2008 | Dekel | G06Q 50/22 382/232 |
| 7,494,338 | B2* | 2/2009 | Durbin | A61C 9/00 433/29 |
| 7,551,720 | B2* | 6/2009 | Schick | A61B 6/14 378/191 |
| 7,600,999 | B2* | 10/2009 | Knopp | A61C 7/146 433/24 |
| 7,966,062 | B2* | 6/2011 | MacAdam | A61B 5/04525 600/523 |
| 7,985,072 | B2* | 7/2011 | Belikov | A61C 19/063 433/215 |
| 8,075,306 | B2* | 12/2011 | Kitching | A61C 7/00 382/128 |
| 8,556,625 | B2* | 10/2013 | Lovely | A61B 5/0088 382/128 |
| 8,647,682 | B2 | 2/2014 | Kunin | |
| 2005/0100333 | A1 | 5/2005 | Kerschbaumer et al. | |
| 2008/0003541 | A1* | 1/2008 | Leslie-Martin | A61O 5/00 433/215 |
| 2008/0009772 | A1* | 1/2008 | Tyler | A61B 5/0492 600/595 |
| 2008/0305454 | A1* | 12/2008 | Kitching | A61C 7/00 433/24 |
| 2009/0029310 | A1* | 1/2009 | Pumphrey | A61C 7/08 433/24 |
| 2011/0243406 | A1 | 10/2011 | Chandler | |
| 2012/0062557 | A1 | 3/2012 | Dillon et al. | |
| 2012/0122053 | A1 | 5/2012 | Hackel et al. | |
| 2012/0288819 | A1 | 11/2012 | Burrell et al. | |
| 2013/0038710 | A1* | 2/2013 | Inglese | A61B 5/0071 348/66 |
| 2013/0051528 | A1 | 2/2013 | Inglese et al. | |
| 2013/0063550 | A1* | 3/2013 | Ritchey | G03B 37/00 348/36 |
| 2013/0078594 | A1* | 3/2013 | Leslie-Martin | A61C 7/08 433/6 |
| 2013/0155249 | A1 | 6/2013 | Neeley et al. | |
| 2013/0218530 | A1* | 8/2013 | Deichmann | A61C 13/0004 703/1 |
| 2013/0218531 | A1* | 8/2013 | Deichmann | A61C 9/004 703/1 |
| 2014/0002364 | A1* | 1/2014 | Ibsies | A61C 19/00 345/168 |
| 2014/0272764 | A1* | 9/2014 | Miller | A61B 1/0684 433/27 |
| 2014/0335469 | A1* | 11/2014 | Boyden | A61B 5/4803 433/27 |
| 2015/0017598 | A1* | 1/2015 | Wu | A61C 9/006 433/29 |

FOREIGN PATENT DOCUMENTS

| | | |
|---|---|---|
| WO | 2008048402 A2 | 4/2008 |
| WO | 2009045286 A1 | 4/2009 |

* cited by examiner

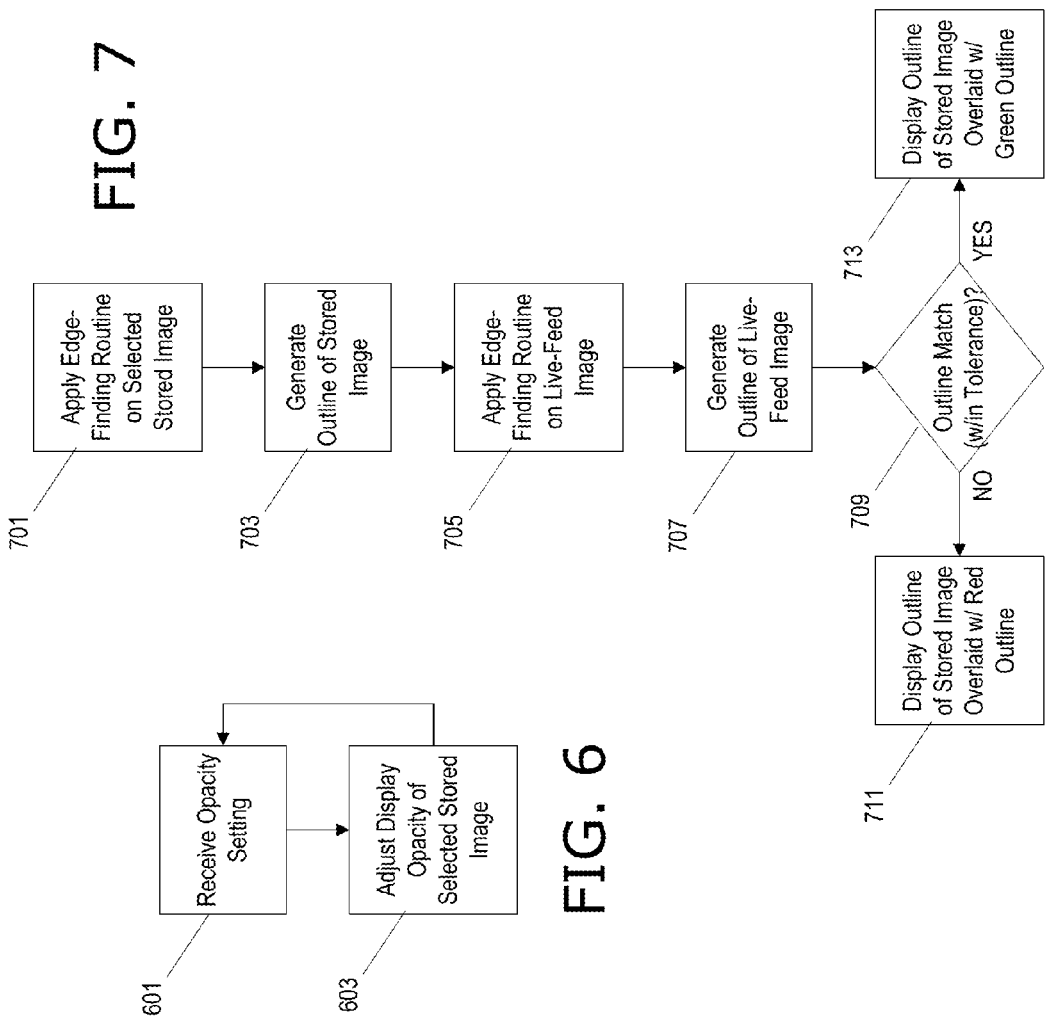
FIG. 7
FIG. 6
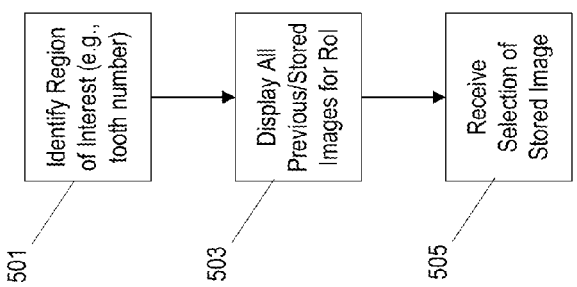
FIG. 5

INTRA-ORAL IMAGE ACQUISITION ALIGNMENT

BACKGROUND

Embodiments of the invention relate to intra-oral image acquisition and, more particularly, methods and systems for improving the alignment between images acquired at two different times.

SUMMARY

Intra-oral imaging may be accomplished with a number of imaging devices (or cameras), including optical imaging devices. For example, laser and infra-red imaging devices are often configured as hand held devices with a wand-like shape. The devices are manipulated by a dentist or dental technician to capture images of the teeth in a patient's mouth. In some situations, it may be beneficial to perform repeated imaging of the same dentition of a single patient. For example, multiple images of a region of interest may be required during follow-up visits to check on the progress of issues and/or treatment. However, hand-held, intra-oral imaging devices require manual manipulation and placement relative to the region(s) of interest. It is often difficult for a human being to manipulate and position a hand-held device in the same manner to capture images from the same focal position so that images of a region of interest acquired two different times are registered and, thus more readily compared.

In one embodiment, the invention provides an intra-oral imaging system including a manually positionable intra-oral image capture device, a display, a processor, and a non-transitory computer-readable memory. Live image data of the patient is received from the intra-oral image capture device and displayed on the display. A previously stored intra-oral image of the patient is accessed from the non-transitory memory and an alignment mask is generated based on the accessed previously stored intra-oral image. The alignment mask is displayed on the display overlaid onto the live image data. The system captures a new intra-oral image of the patient from the live image data and stores the new intra-oral image to the non-transitory memory.

In another embodiment, the invention provides a method of aiding alignment of a manually positionable intra-oral image capture device. The method includes receiving live image data of a patient from the intra-oral image capture device and displaying the live image data on a display. A previously stored intra-oral image of the patient is accessed from memory and an alignment mask is automatically generated based on the accessed previously stored image. The alignment mask is displayed overlaid onto the live image data. A new intra-oral image of the patient is captured from the live image data and stored to memory.

In yet another embodiment, the invention provides an intra-oral imaging system that includes a manually positionable hand-held infrared intra-oral image capture device. The intra-oral image capture device is configured to project infrared light onto a tooth and capture an image of at least a portion of the tooth illuminated with the projected infrared light. Live image data of the patient is received from the intra-oral image capture device and displayed on a display. A previously stored intra-oral image of the patient is accessed from memory. An edge-finding routine is applied to both the stored image and the live image to generate a pair of outlines of at least a portion of a tooth from each respective image. The system determines whether the first outline matches the second outline and displays the alignment mask overlaid onto the live image data. The system also provides a visual indication on the display when the system determines that the outlines match. For example, in some embodiments, the visual indication is provided by displaying the outline in a first color when the outlines match and displaying the outline in a second color when the outlines do not match.

In still other embodiments, the invention provides an intra-oral imaging system that includes a manually positionable hand-held intra-oral image capture device. Live image data is received from the intra-oral image capture device and displayed on a display. A previously stored intra-oral image of the patient is accessed from a non-transitory memory and displayed on the display overlaid onto the live image data. The system also captures a new intra-oral image of the patient from the live image data and stores the new intra-oral image to the non-transitory memory.

Other aspects of the invention will become apparent by consideration of the detailed description and accompanying drawings.

BRIEF DESCRIPTION OF THE DRAWINGS

FIG. 5 is a flowchart of a method for selecting a stored image to use as an alignment mask in the method of FIG. 4.

FIG. 6 is a flowchart of a method for adjusting the display of the alignment mask in the method of FIG. 4.

FIG. 7 is a flowchart of a method for displaying the alignment mask in the method of FIG. 4 in a way that provides visual alignment feedback to the user.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It should also be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include standard processing components, such as one or more processors, one or more memory modules including non-transitory computer-readable medium, one or more input/output interfaces, and various connections (e.g., a system bus) connecting the components.

Figure 1A:
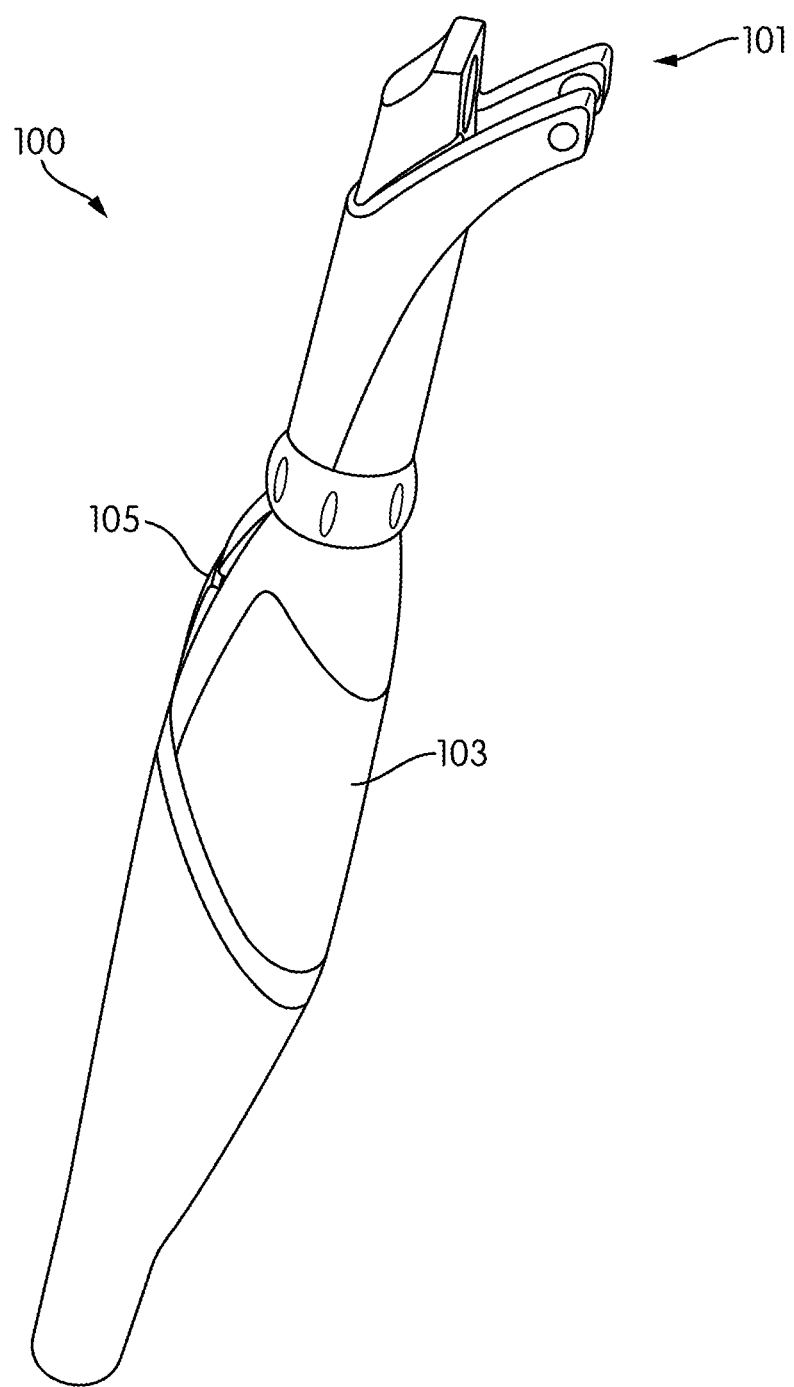
FIG. 1A is a perspective view of an intra-oral imaging device according to one embodiment.
Figure 1B:
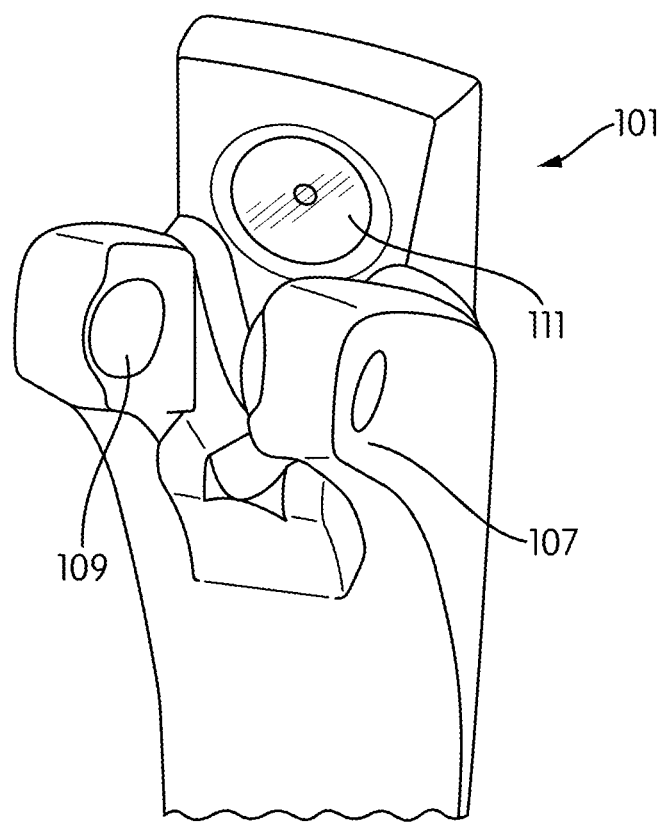
FIG. 1B is a perspective view of the distal head of the intra-oral imaging device of FIG. 1A.

FIG. 1A illustrates an example of a hand-held infrared intra-oral imaging device. The device 100 includes in an imaging head 101 that is inserted into the oral cavity of a patient and a handle 103 that is held in the hand of a dentist professional (e.g., a dentist). A button 105 is positioned on the rear side of the handle 103. FIG. 1B shows the imaging head 101 in further detail. The head 101 includes a pair of arms 107 that are spaced to fit on either side of a patient's tooth. An infrared light source 109 is positioned on each arm 107 and oriented to illuminate a tooth with infrared light when the device 100 is appropriately positioned around the patient's tooth. A camera (not pictured) positioned within the housing of the device captures an image of the illuminated tooth through a lens 111 that is positioned adjacent to the opening between the two arms 107. In some constructions, the camera is configured to capture an image in response to the button 105 being pressed by the user.

Figure 2:
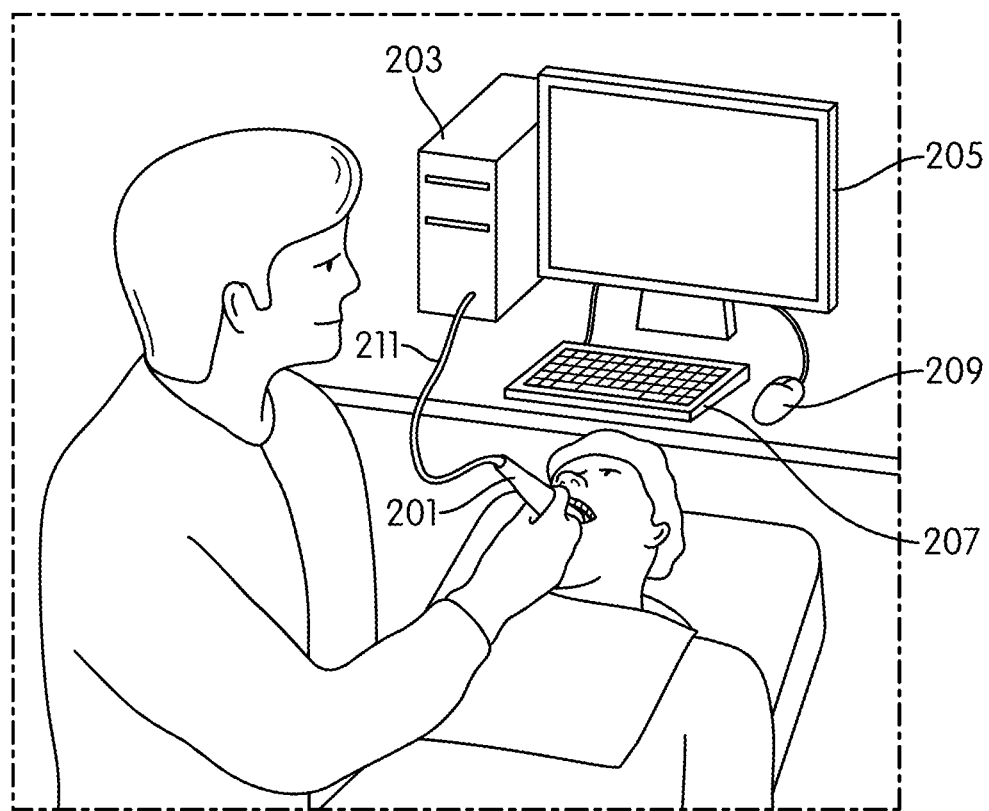
FIG. 2 is a perspective view of a dental professional using the intra-oral imaging device of FIG. 1A to capture images of a patient's teeth.

FIG. 2 shows an example of one such handheld device in use and illustrates additional components of an imaging system that includes a handheld device like the one shown in FIGS. 1A and 1B. As shown in FIG. 2, the handheld device 201 is coupled to a computer 203 by a cable 211. In this example, the computer 203 includes a standard desktop computer system executing software instructions that provide the functionality described herein. However, in other constructions, the computer 203 can be replaced with a specially adapted system that is configured to perform the functions described herein—for example, a system that includes a processor and a non-transient computer-readable memory that stores instructions that are executed by the processor. The computer 203 is also coupled to a display screen 205, a keyboard 207, and a mouse 209.

As discussed in further detail below, the system also stores previously captured images that will be used to assist with alignment of the handheld imaging device. These dental images may be stored on the same memory as the computer-readable instructions or they can be stored on a separate dedicated non-transitory computer-readable memory. For example, in some systems, the dental images are stored on a remote server or cloud computing environment while the executable instructions that provide the functionality described herein are stored on a local memory device. Therefore, unless otherwise specified, the term "memory" as used herein may be interpreted as a single physical memory unit or multiple separate physical memory units.

During use, the dental professional holds the device 201 in her hand by the handle and places the imaging head in the mouth of the patient such that one or more of the patient's teeth are positioned between the arms and illuminated by the infrared light sources. Live image data, captured by the camera positioned within the device 201, is transmitted through the cable 211 to the computer 203. The live image data is then shown on the display screen 205 and is viewable in real-time by the dental professional. Using various input controls—for example, the keyboard 207 and mouse 209, the dental professional can also access previously stored images and cause them to be shown on the display screen 205.

The infrared device and the system illustrated in FIG. 2 provide a dental professional with real-time imaging data without prolonged (or any) exposure to the radiation that would be generated by an x-ray system. The dental professional can also capture additional images for later retrieval and analysis. A more detailed example of the handheld device illustrated in FIGS. 1A, 1B and 2 is the DEXIS CariVu™ and is described in further detail in U.S. Publication No. 2012/0122053, the entire contents of which is incorporated herein by reference.

Figure 3:
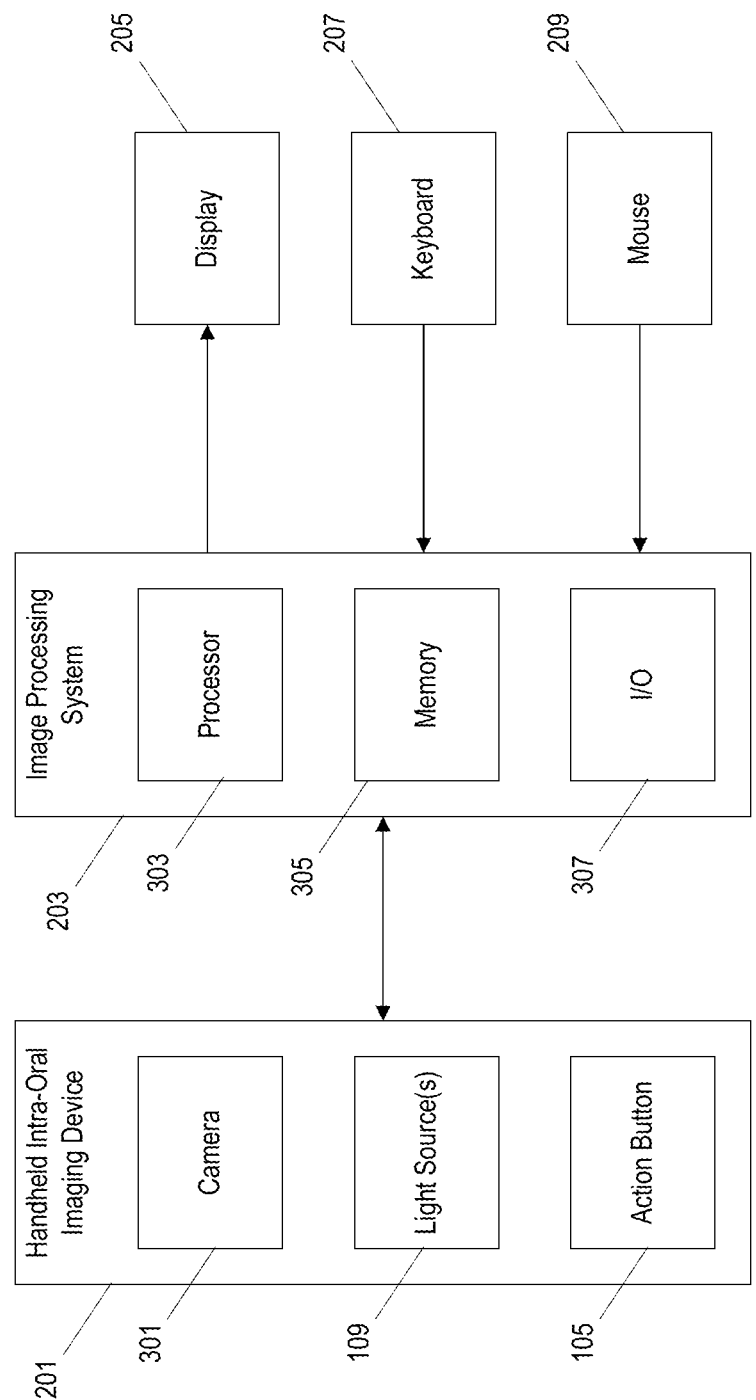
FIG. 3 is a block diagram of the imaging system of FIG. 2 including the intra-oral imaging device of FIG. 1A.

FIG. 3 illustrates the components of the system of FIG. 2 is block-diagram format. The handheld intra-oral imaging device 201 includes one or more light sources 109 and an action button 105 as well as an internal camera 301 for capturing images. The handheld intra-oral imaging device 201 is in two-way communication with an image processing system 203 (e.g., the computer 203 of FIG. 2). Although the example shown in FIG. 3 provides for two-way communication, in some other constructions, the handheld device 201 may communicate only in one direction (i.e., sending image data captured by the camera 301 to the image processing system 203).

As described above, the image processing system 203 may be implemented on a desktop computer system or can be implemented as an application-specific, stand-alone system. The image processing system 203 of this example includes a processor 303 and a memory 305. As discussed above, the memory 305 is a non-transient computer-readable memory that stores instructions which are executed by the processor 303 to provide the system functionality described herein. The image processing system 203 also includes an input/output interface 307 to implement communication with the handheld intra-oral device 201 and other external systems and peripherals. For example, through the I/O interface 307, the image processing system 203 sends image data to be shown on the display 205 and receives user inputs from an attached keyboard 207 and mouse 209.

Among other things, the image processing system 203 is configured to assist the dental professional in capturing a series of images from the same perspective so that the series of images can be analyzed and evaluated to monitor the progression of various dental conditions. However, because the imaging device is handheld, proper, repeatable, and reliable placement of the device by the dental professional is a challenge. Therefore, the image processing system 203 is configured to provide interactive user guidance to assist and, in some cases, ensure that proper alignment with one or more previously stored images is achieved.

Figure 4:
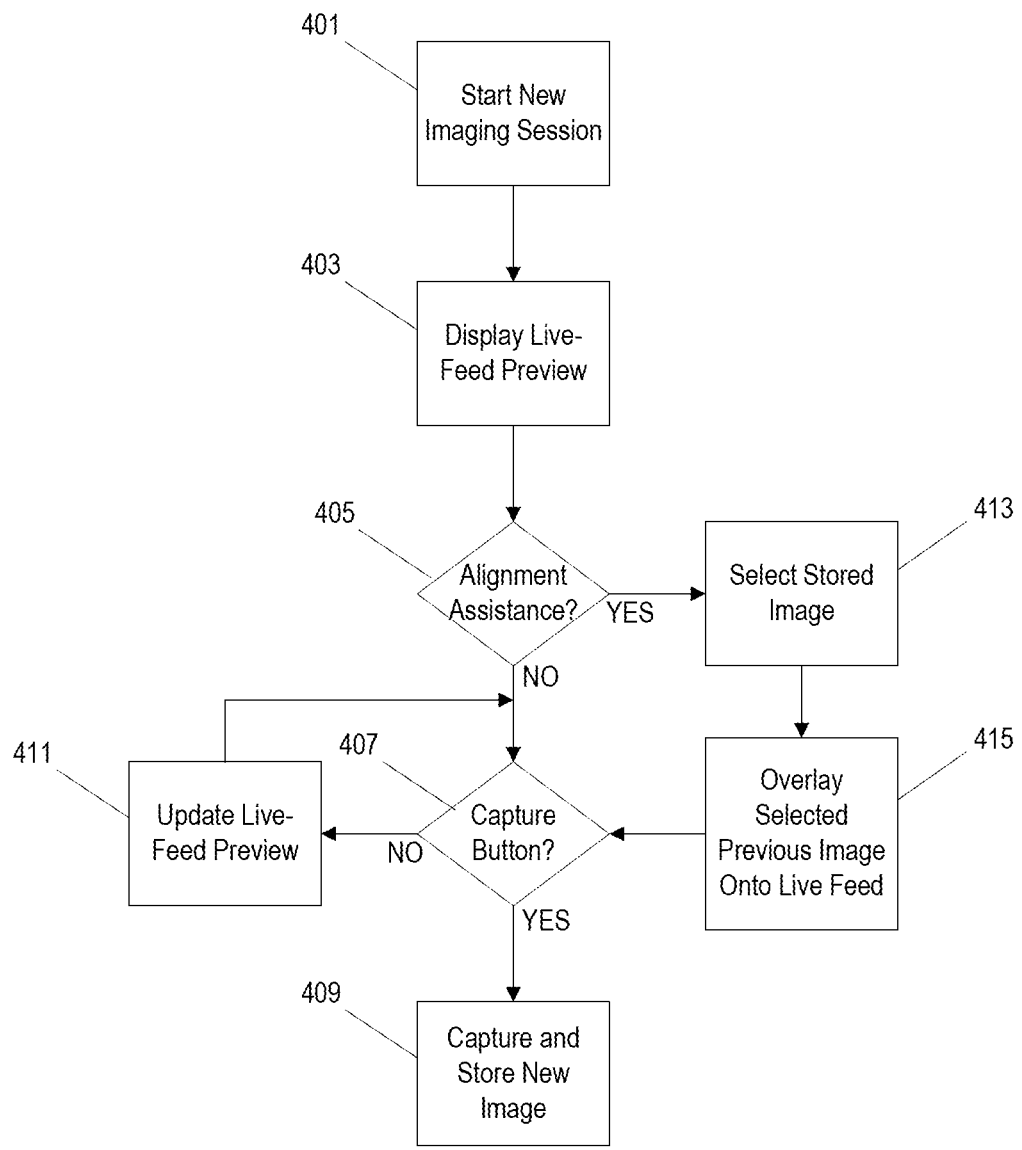
FIG. 4 is a flowchart of a method for acquiring intra-oral images using the imaging system of FIG. 2.

FIG. 4 illustrates an example of one method implemented by the image processing system 203 to assist with alignment of the handheld device. When a new imaging session is started (step 401) a live-feed preview of the image captured by the handheld device is shown on the display screen (step 403). This live-feed image data is captured by the camera positioned within the handheld tool and transmitted to the image processing system by a wired or wireless communication interface. In this example, the alignment assistance feature is optional and, therefore, if alignment assistance is turned off (step 405), the image processing system simply monitors for a signal from the handheld device indicating that the "capture" button positioned on the device has been pressed (step 407). When the button has been pressed, the image processing system captures and stores a new image from the live-feed image data received from the handheld device (step 409). If the capture button has not been pressed, the image processing system continues to update and display the live-feed preview on the display screen (step 411).

When the alignment assistance feature is activated (step 405), the image processing system prompts the user to select a previously stored image from memory (step 413) and uses the selected image to generate an alignment mask that is displayed as overlaid onto the live-feed image data on the display screen (step 415). With the previous image overlaid the live-feed image, the user can continually adjust the position and orientation of the handheld imaging device until the live-feed image matches the previously stored image. In the example of FIG. 4, the system continues to update the live-feed image (step 411) until the user presses the capture button (step 407) causing the system to capture and store a new image (step 409). However, in some constructions, as discussed further below, the system may be configured to automatically capture the new image from the live-feed data when certain preconditions are satisfied.

In some constructions, the prompt displayed by the system instructing the user to select a previously stored image simply provides access to a file explorer window. The user could then define their own hierarchical file structure including, for example, a separate folder for each patient and one or more subfolders for each patient identifying a specific tooth or "region of interest." In other constructions, the user identifies the patient while initiating a new imaging session and, therefore, the prompt only displays a series of prior images corresponding to that specific patient. In still other constructions, as illustrated in FIG. 5, the system prompts the user to identify a specific region of interest (e.g., a tooth number) (step 501) and displays a list of all previously stored images for the specified region of interest (step 503). As a result, the user is only able to select stored images corresponding to the identified region of interest to serve as an alignment mask (step 505).

In some constructions, the alignment mask is generated simply as a copy of the previous image displayed onto the same window as the live feed data. However, in some examples, as shown in FIG. 6, the user is able to identify an opacity setting (step 601) and the display opacity of the previously stored image is adjusted (step 603) so that the live-feed image data becomes more visible to the user. In some constructions, the opacity setting can be adjusted by the user (using, for example, a slider-bar or other control shown on a graphical user interface on the display screen) throughout the image acquisition process and the display opacity of the alignment mask (i.e., the partial transparent previously stored image) will be adjusted in near-real-time. In other constructions, the opacity setting is pre-defined on the system and is not adjustable by the user.

Other constructions of the system can be configured to utilize still other types of alignment masks. For example, the system may be generated to define an outline of the tooth and display only the outline of the tooth from the prior image overlaid onto the live feed data. Furthermore, in some constructions, the user can select between a plurality of available alignment masks to suit their preference or based on the content and characteristics of the live-feed data or the previously stored image. Additionally, as noted above, some constructions of the system are configured to analyze the degree of alignment between the live feed data and the previously stored image and to automatically capture and store an image from the live-feed data when certain conditions are satisfied.

FIG. 7 illustrates a method for providing alignment assistance using the system of FIG. 2 utilizing an outline of the teeth from the previously stored image as the overlaid alignment mask, automatically notifying the user when proper alignment is achieved, and, in some cases, automatically capturing an image from the live-feed data when proper alignment is detected. After the user has selected a previously stored image to serve as the alignment mask, the system applies an edge-finding routine on the selected stored image (step 701) and generates an outline of the teeth from the stored image (step 703). The same edge-finding routine is periodically applied to the live-feed image data (step 705) to generate an outline of the teeth from the live-feed data (step 707).

The system compares the two generated outlines to determine whether they "match" within a defined tolerance range (step 709). For example, the system may conclude that the outlines "match" if no pixel from the live-feed outline is further than a defined distance from a pixel of the previously stored image outline. Such a simplified routine would not necessarily require markers or registration. However, in some cases the automatic alignment detection mechanism might be more susceptible to changes in tooth shape rendering a match more difficult or impossible. More advanced "match" detection routines may be implemented to identify specific features that are common to both images (e.g., the upper corners of the tooth or a filling) and use these common features as "markers" to provide more advanced alignment analysis.

Whichever mechanism is employed to determine whether the live-feed outline matches the previously stored image outline (step 709), the system shows the live-feed image data on the display screen with the previously stored image outline overlaid onto the live-feed image as the alignment mask. When a "match" is not detected and the system determines that the live-feed data is not in alignment with the previously stored image, the system displays the alignment mask outline in a first color (e.g., red) (step 711). When a "match" is detected and the system determines that the live-feed data is in proper alignment with the previously stored image, then the alignment mask outline is displayed in a second color (e.g., green) (step 713).

In some constructions, the change in color of the alignment mask or another audio or visual prompt is generated to instruct the user to press the action button and to capture an image from the live-feed data. However, in some constructions, the system may be configured to automatically capture and store an image from the live-feed image data as soon as proper alignment is detected. In still other constructions, the system may allow the user to select whether an image is to be captured automatically when alignment is detected or whether the user will be required to press the "capture" button in order to capture and store an image from the live-feed image data.

As discussed above, various constructions of the systems described herein may have different alignment masks that are generated and displayed overlaid onto the live-feed data. FIGS. 8-12 illustrate examples of graphical user interfaces that are displayed to the user on the display screen at various points during the alignment process.

Figure 8:
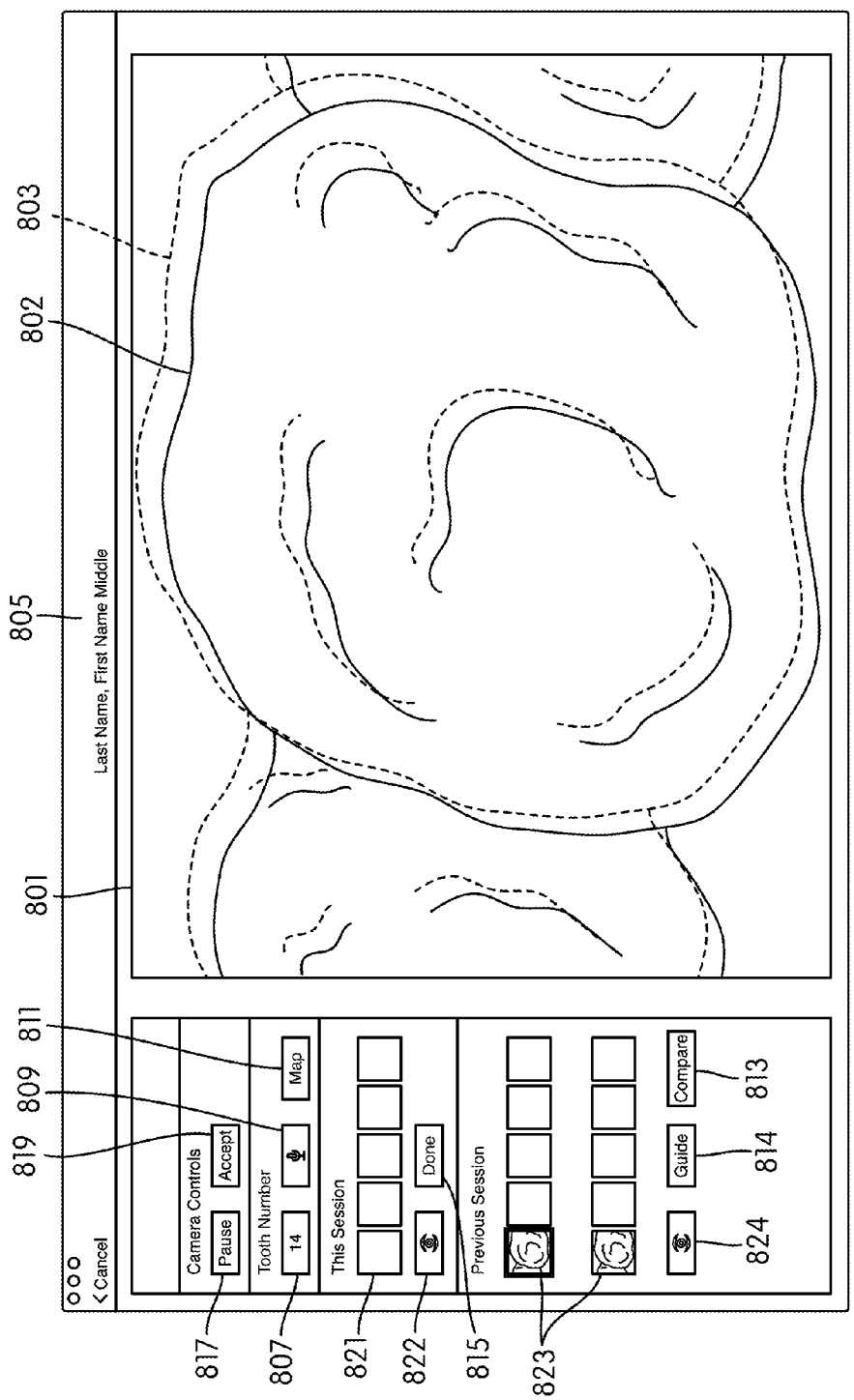
FIG. 8 is a graphical user interface of the imaging system of FIG. 2 using a partially transparent alignment mask with the imaging device of FIG. 1A positioned out of alignment.
Figure 9:
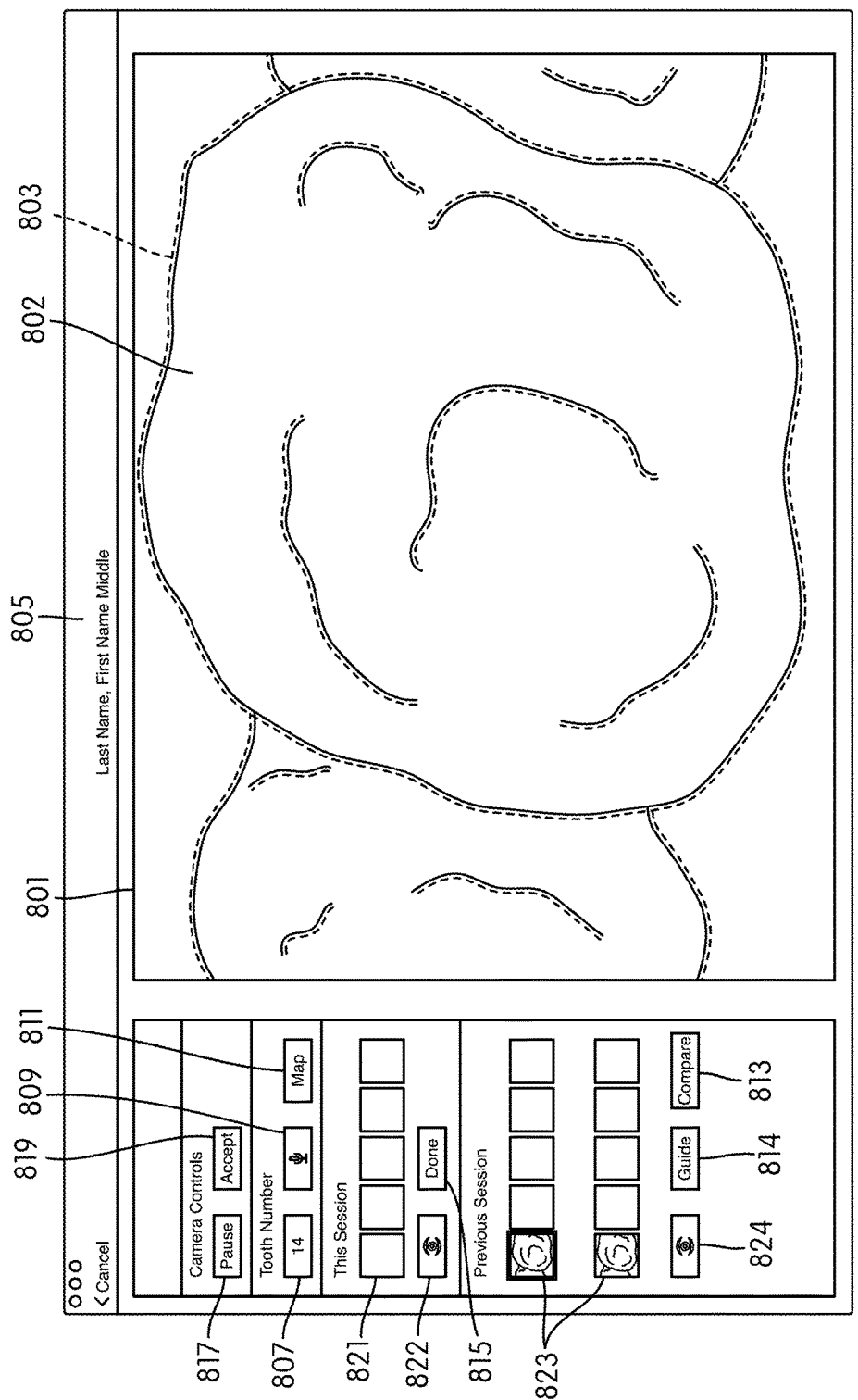
FIG. 9 is a graphical user interface of the imaging system of FIG. 2 using a partially transparent alignment mask with the imaging device of FIG. 1A positioned in proper alignment.

FIGS. 8 and 9 illustrate an example of a graphical user interface shown on the display screen (e.g., display screen 205) that utilizes a partially transparent version of the stored image as the alignment mask. The displayed user interface includes a single image frame 801 that displays live image data 802. The previously stored image 803 is also displayed in the same window and is made partially transparent to serve as a stationary alignment mask. As discussed above, the opacity of the alignment mask may be set according to a previously defined setting (e.g., a static system setting or a user adjustable setting). Alternatively, although not illustrated in this example, an adjustment control can be included in the displayed user interface to allow the user to adjust the opacity of the alignment mask in near real-time. Furthermore, although this example shows the live feed image displayed without transparency and the alignment mask shown as partially transparent, in other constructions of the system, the alignment mask may be shown without transparency while the live feed image is shown as partially transparent. In still other constructions, the user is able to select whether the alignment mask or the live feed image is shown as partially transparent based on their own preference.

The displayed user interface in FIGS. 8 and 9 includes header bar 805 that displays the name of the patient and a series of controls that allow the user to select a "region of interest" for the imaging session. Labeled with the heading "Tooth Number," these controls can optionally include a "microphone" button 809 that, when selected, allow the user to specify a tooth number verbally. The "Tooth Number" controls can also include a "map" button 811 that, when selected, causes a complete map of the dental arch to be shown on the screen. The user can then select a specific tooth by clicking on the appropriate location on the displayed map. Once a region of interest is selected, the user interface displays the selected tooth number in the "tooth number" field 807. In some embodiments, the user may also define a specific region of interest by entering a tooth number directly into the "tooth number" field 807 using a keyboard. As discussed in further detail below, identifying the region of interest (i.e., a specific tooth number) limits the available prior images that may be selected from for use as an alignment mask, thus making it easier for the user to find a suitable image for the alignment mask. In this example, the identified tooth number will also be appended to any new captured images as metadata to categorize the image, for example, for possible future use as an alignment mask.

The user interface also includes various camera controls. For example, as noted above, the live feed image 802 displayed in the image frame 801 is generally updated in real-time or near real-time. The user interface of FIGS. 8 and 9 includes a pause button 817 that can stop the live feed and display a static image from the live feed data. Once the live feed is paused, the user can then press the "accept" button 819 to cause the displayed image from the live feed data to be stored as a new image file. A thumbnail scroll control 821 shows thumbnails of new images that have been captured (e.g., "accepted") during the current imaging session. A user may also view one of the recently captured images in the image frame 801 by selecting one of the thumbnail images in the scroll 821 and may selectively apply an image processing filter by selecting button 822. After capturing images, the user can terminate the imaging session by selecting the "done" button 815.

As noted above, the alignment mask 803 used in the examples of FIGS. 8 and 9 is a partially transparent version of another image captured during a prior imaging session. The user interface of FIGS. 8 and 9 displays a series of thumbnail scroll controls 823 displaying thumbnail versions of images of the same patient corresponding to the same defined region of interest captured during previous imaging sessions. The example of FIGS. 8 and 9 includes two separate scrolls 823 that each show all images for the region of interest captured during each of two prior imaging sessions. All images captured during the most recent prior session are shown in the top scroll control 823 and all images captured during another, even earlier session are shown in the bottom scroll control 823.

The user is also able to view the images from the prior sessions in their unaltered form (i.e., not as an alignment mask) by selecting a thumbnail of one of the prior images in either scroll control 823 and clicking on the "compare" button 813. Selecting the "compare" button 813 causes a second image frame to be displayed (for example, as in FIG. 12 below) so that the prior image can be viewed next to the live feed image. The user may again selectively choose to apply an image processing filter to the prior stored image by selecting button 824. When a prior image is identified that the user would like to use as the alignment mask, the user selects the "guide" button 814. Selecting the "guide" button 814 causes an alignment mask 803 corresponding to the selected thumbnail from scroll control 823 to be generated and displayed overlaid onto the live feed image data 802 in the image frame 801.

In addition to displaying an alignment mask 803 overlaid onto live image data 802 in the image frame 801, the system illustrated in FIGS. 8 and 9 can be used to display an alignment mask 803 displayed overlaid onto a still image that has been captured during the current imaging session. To do this, the user would select a captured image from thumbnail scroll control 821 causing the newly captured still image to be shown in image frame 801. The user would also select a prior captured image from one of the thumbnail scroll controls 823 and select the "guide" button 814. The system would then generate an alignment mask 803 for the selected thumbnail from scroll control 823 and would display the alignment mask 803 in the image frame 801 overlaid onto the still image from the current imaging session corresponding to the selected thumbnail from scroll control 821. In this way, after a still image is captured in the current imaging session, the user can continue to generate additional alignment masks based on other prior images to ensure that the newly captured image aligns not only with one selected prior image, but also with a series of other prior images.

As discussed above, the use of the partially transparent prior image as an alignment mask allows the user to determine whether the handheld device is positioned so that new captured images are properly aligned with the previously captured image. The images shown in the image frame 801 in FIG. 8 indicate that the live feed data is not in proper alignment with the previously stored data. Based on the displayed image, the user knows that the position of the handheld device must be further adjusted before capturing a new image—i.e., the user must move the handheld device around until the live image data 802 lines up with the alignment mask 803. In some constructions, the system may be configured to provide on-screen instructions or audio cues to instruct the user on how to move the handheld device to place it in proper alignment. FIG. 9 shows the live feed data and the alignment mask in proper alignment.

Figure 10:
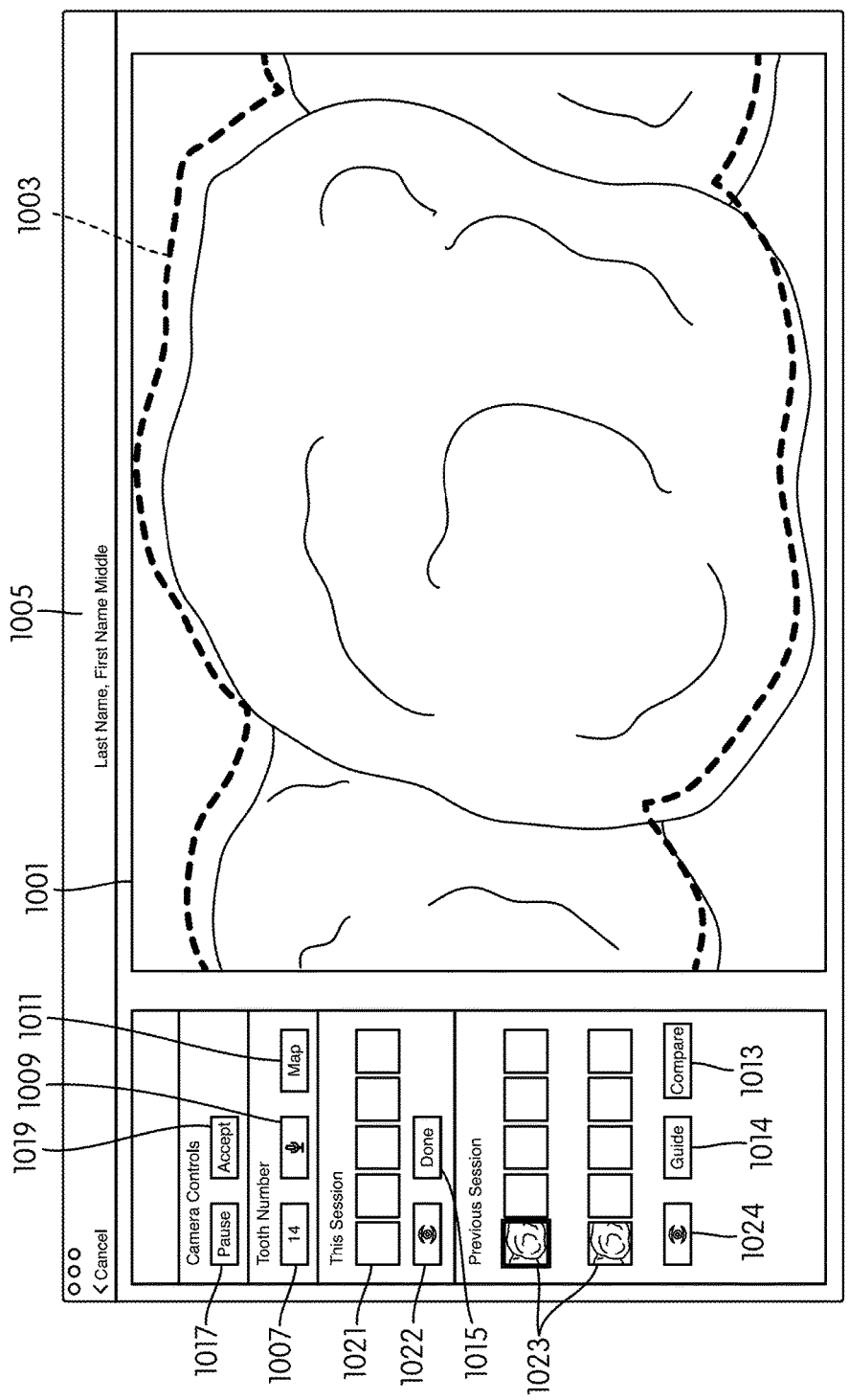
FIG. 10 is a graphical user interface of the imaging system of FIG. 2 using an outline alignment mask with the imaging device of FIG. 1A positioned out of alignment.
Figure 11:
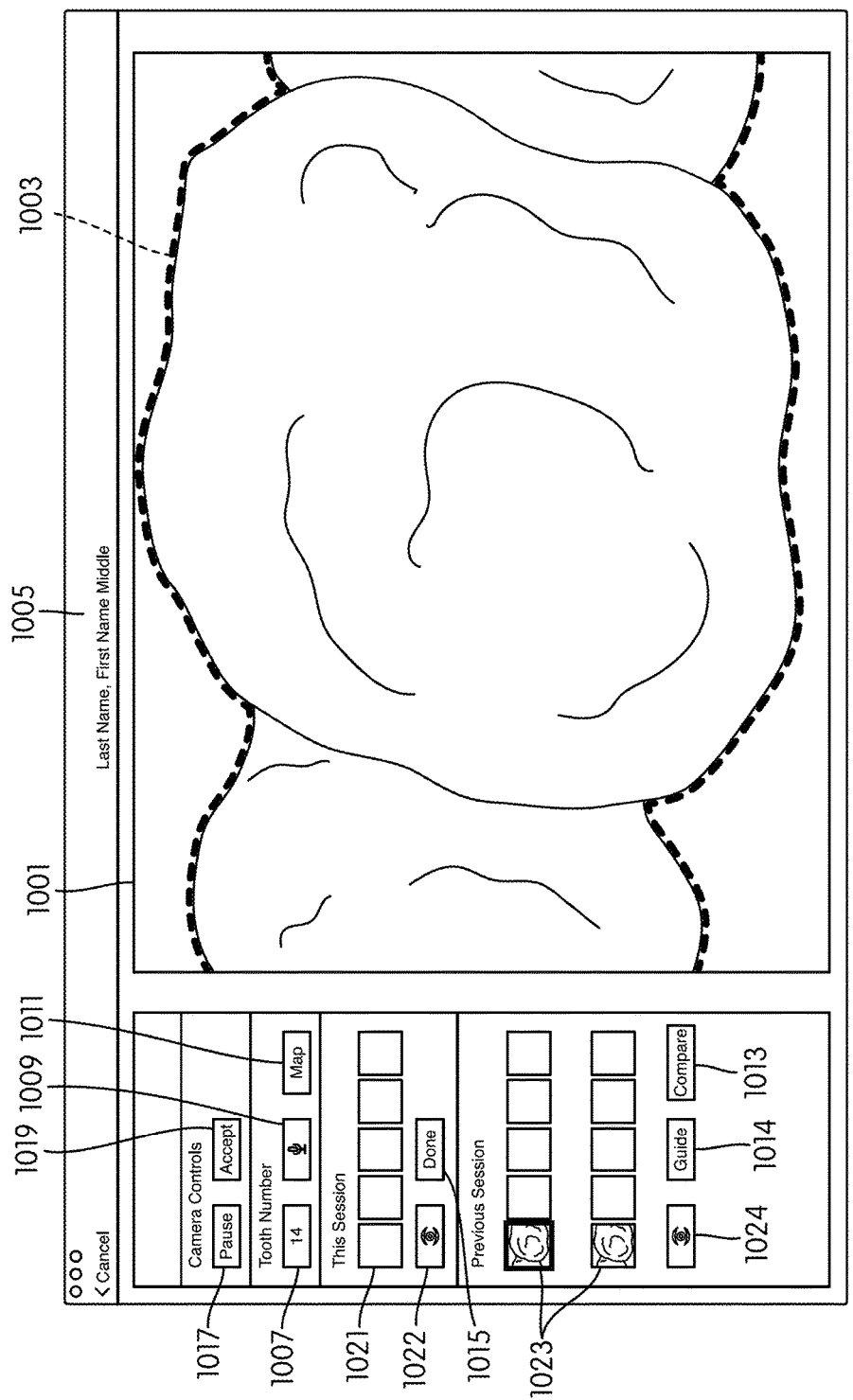
FIG. 11 is a graphical user interface of the imaging system of FIG. 2 using an outline alignment mask with the imaging device of FIG. 1A positioned in proper alignment.

FIGS. 10 and 11 illustrate an example of a similar graphical user interface shown on the display screen (e.g., display screen 205) that utilizes an outline of the teeth from the previously stored image as the alignment mask. This graphical user interface also includes an image frame 1001 that displays live feed image data from the handheld device and also displays an outline 1003 generated by the edge-finding routine performed on the previously stored image. Like the example of FIGS. 8 and 9, the user interface of FIGS. 10 and 11 includes a header bar 1005, a "tooth number" field 1007, an audio control (for verbally selecting a tooth number) 1009, a map button 1011, a compare button 1013, a guide button 1014, a "done" button 1015, a pause button 1017, and an accept button 1019. The user interface of FIGS. 10 and 11 also includes a current session image thumbnail scroll control 1021, a current session image filter/processing button 1022, one or more previous session image thumbnail scroll controls 1023, and a previous session image filter/processing button 1024. Except as otherwise specified, the various controls and displays in the user interface example of FIGS. 10 and 11 have the same purpose and provide the same functionality as the similarly named and labeled features in the example of FIGS. 8 and 9.

Again, the alignment mask 1003 overlaid onto the live feed image data (or a still image captured during the current imaging session) in the display frame 1001 allows the user to determine whether proper alignment has been achieved. FIG. 10 shows the live feed image data out of alignment with the alignment mask 1003 while FIG. 11 shows the live feed image data in proper alignment with the alignment mask 1003. As noted above, various visual, haptic, and audio cues may be generated to indicate to the user whether proper alignment has been achieved. For example, in FIG. 10, the alignment mask outline 1003 is displayed in a first color (e.g., red) to indicate that the live feed image is not aligned with the alignment mask 1003. Conversely, in the example of FIG. 11, the alignment mask outline 1003 is displayed in a second color (e.g., green) to indicate that the live feed image is aligned with the alignment mask 1003 and, therefore, the handheld device is properly positioned and oriented. Optionally, alignment (or lack thereof) can also be indicated by an audible tone and/or a vibration of the handheld device.

Figure 12:
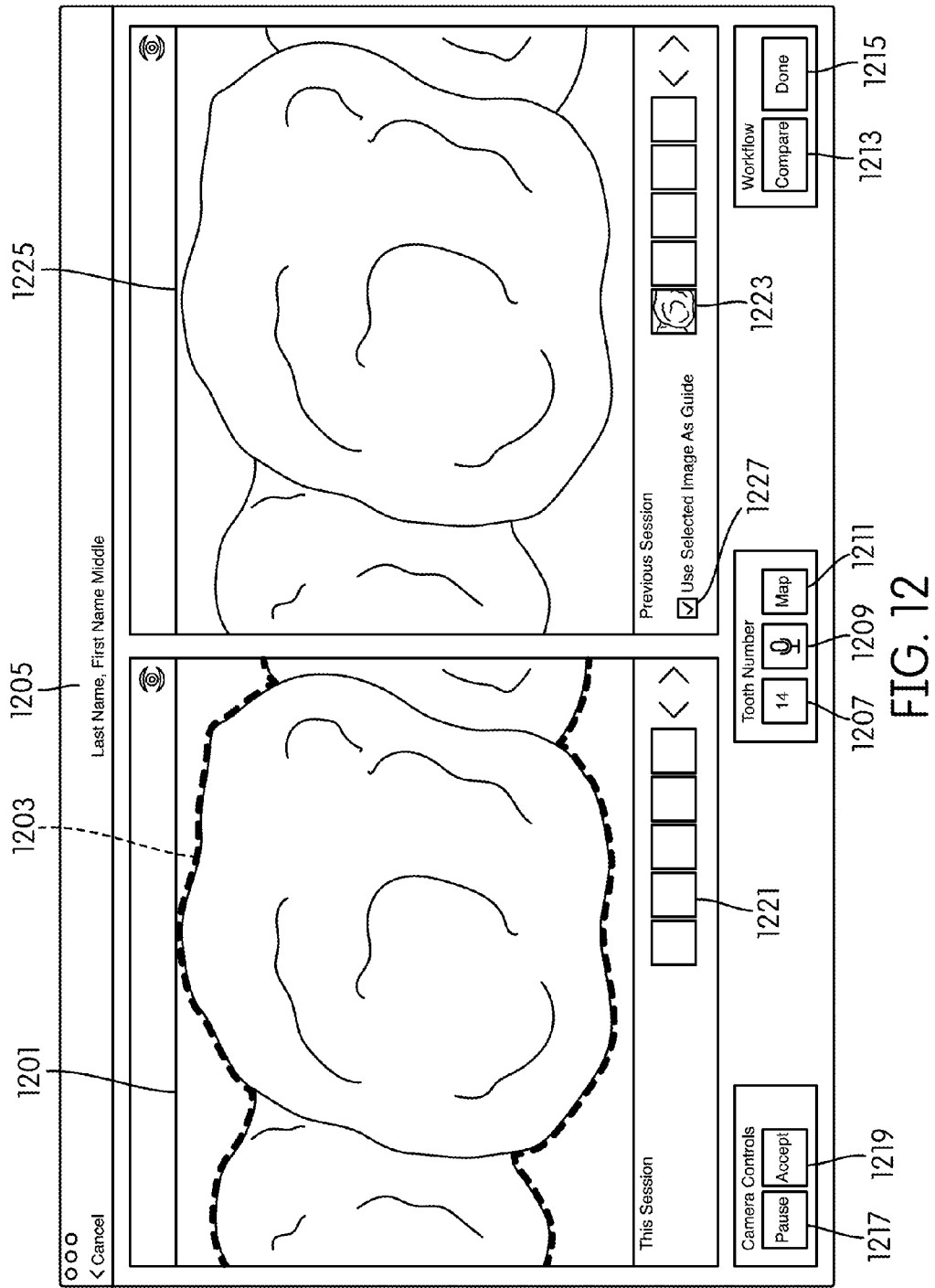
FIG. 12 is a graphical user interface of the imaging system of FIG. 2 showing the alignment mask overlaid onto a live image feed and showing the source image for the alignment mask in its unaltered form.

FIG. 12 illustrates another example of a user interface that provides alignment assistance. Like the example of FIGS. 10 and 11, the user interface of FIG. 12 includes an image frame 1201 that displays live image data received from the handheld device and an outline alignment mask 1203. This user interface also includes a header bar 1205, a "tooth number" field 1207, an audio control (for verbally indicating a tooth number) 1209, a map button 1211, a compare button 1213, a "done" button 1215, a pause button 1217, an accept button 1219, and a thumbnail scroll 1221 as described above.

The user interface of FIG. 12 also includes an additional image frame 1225 displayed to the right of the live image feed frame 1201. In this second image frame 1225, the user is able to view previously stored, unaltered images at the same time as the live feed image data (or a new captured image from the current imaging session) is displayed in the live image feed frame 1201. A thumbnail scroll 1223 positioned below the second image frame 1225 displays thumbnail versions of all previously stored images that correspond to both the patient name (identified in the header bar 1205) and the region of interest (identified by the "region of interest" control 1207). When the user selects one of the thumbnails from this second thumbnail scroll 1223, the corresponding image is displayed in the second image frame 1225. To designate a previously stored image to be used as the basis for the alignment mask outline 1203, the user must also select the check box 1227 positioned next to the second thumbnail scroll 1223. In this way, the user can view the live feed image data, the paused image, or new images captured during the current imaging session displayed next to any of a plurality of previously stored images. Furthermore, once a previously stored image is selected to serve as the alignment mask, the user can continue to view other previously stored images (in the second image frame 1225) without changing the alignment mask 1203 that is displayed on the live feed image (in the first image frame 1201).

In some systems, the user interface of FIG. 12 is used as the standard interface and is constantly displayed to the user in all imaging sessions. In other systems, the user interface of FIG. 12 is displayed only when the user selects the "compare" button in a single image frame user interface (e.g., FIGS. 8-11) causing the second image frame to be shown. In systems that implement a user interface that can selectively toggle between a single image frame and a dual image frame view, the user can return to the single image frame view by deselecting the "compare" button 1213 or, in some systems, by pressing the "done" button 1215.

Although the systems described herein primarily focus on the overlay of an alignment mask (e.g., a partial transparent image or an outline) onto live-feed image data, the display screen can be used to provide other information to support the user's in achieving proper positioning and orientation of the imaging device. It may also provide additional information that can help the user in evaluating a dental condition of the patient.

For example, the brightness and contrast of the captured image can be affected by the degree to which the imaging device is pressed against the surface of the tooth (i.e., the applied pressure). Depending on the type of alignment mask that is utilized, it can be difficult or impossible to evaluate whether proper pressure is applied and the brightness/contrast are appropriately matched between the live-feed data and the stored image. Among other benefits, the side-by-side configuration of the user interface of FIG. 12 allows the user to evaluate brightness and contrast characteristics. Using this interface, the user is able to evaluate proper orientation and positioning of the image device by using the left portion of the screen and can monitor an evaluate pressure and brightness characteristics by visually comparing the live-feed image data on the left of the screen to the previously stored image on the right side of the screen.

Thus, the invention provides, among other things, a system and method for assisting a dental professional in capturing a series of dental images with proper consistent alignment using a handheld dental imaging device. Various features and advantages of the invention are set forth in the following claims.

What is claimed is:
1. An intra-oral imaging system comprising:
   a manually positionable intra-oral image capture device;
   a display;
   a processor coupled to the intra-oral image captured device and the display; and a non-transitory memory coupled to the processor and
storing instructions that, when executed by the processor, cause the system to
receive live image data of a patient from the intra-oral image capture device,
display the live image data on the display,
access a previously stored intra-oral image of the patient from the non-transitory memory,
generate an alignment mask based on the accessed previously stored intra-oral image,
display the alignment mask on the display overlaid on the live image data,
capture a new intra-oral image of the patient from the live image data, and
store the new intra-oral image to the non-transitory memory, display the new intra-oral image on the display, or both.

2. The intra-oral imaging system of claim 1, wherein the instructions, when executed by the processor, further cause the system to determine whether the live image data is aligned with the alignment mask.

3. The intra-oral imaging system of claim 2, wherein the instructions, when executed by the processor, further cause the system to display visual feedback on the display in response to determining that the live image data is aligned with the alignment mask.

4. The intra-oral imaging system of claim 2, wherein the instructions, when executed by the processor, cause the system to automatically capture the new intra-oral image of the patient from the live image data in response to determining that the live image data is aligned with the alignment mask.

5. The intra-oral imaging system of claim 1, wherein the instructions, when executed by the processor, further cause the system to
receive a user input, and
capture the new intra-oral image from the live image data in response to receiving the user input.

6. The intra-oral imaging system of claim 1, wherein the instructions, when executed by the processor, further cause the system to apply an edge-finding routine to generate a first outline of at least a portion of a tooth in the accessed previously stored intra-oral image of the patient.

7. The intra-oral imaging system of claim 6, wherein the instructions, when executed by the processor, cause the system to generate the alignment mask based on the first outline.

8. The intra-oral imaging system of claim 6, wherein the instructions, when executed by the processor, further cause the system to
determine whether the live image data is aligned with the alignment mask,
display the alignment mask on the display in a first color when the system determines that the live data is not aligned with the alignment mask, and
display the alignment mask on the display in a second color when the system determines that the live data is aligned with the alignment mask.

9. The intra-oral imaging system of claim 8, wherein the instructions, when executed by the processor, further cause the system to apply the edge-finding routine to generate a second outline of at least a portion of a tooth in the live image data, and cause the system to determine whether the live image data is aligned with the alignment mask by determining whether the first outline matches the second outline.

10. The intra-oral imaging system of claim 1, wherein the instructions, when executed by the processor, cause the system to display the alignment mask on the display overlaid on the live image data by displaying a partially transparent version of the accessed previously stored intra-oral image overlaid on the live image data.

11. The intra-oral imaging system of claim 1, wherein the instructions, when executed by the processor, further cause the system to
display a list of previously stored intra-oral images for the patient,
receive a selection from a user of a previously stored intra-oral image from the list, and
generate the alignment mask based on the selected previously stored intra-oral image.

12. The intra-oral imaging system of claim 11, wherein the instructions, when executed by the processor, further cause the system to
identify a region of interest within an oral cavity of the patient, and
generate the list of previously stored intra-oral images for the patient, wherein the generated list includes only previously stored intra-oral images that correspond to the identified region of interest.

13. The intra-oral imaging system of claim 1, wherein the live image data displayed on the display is a real-time feed of images captured by the intra-oral image capture device as a position and orientation of the intra-oral image capture device is manually adjusted by a user.

14. The intra-oral imaging system of claim 1, wherein the non-transitory memory further includes a first memory unit and a second memory unit, wherein the instructions are stored on the first memory unit, and wherein the instructions, when executed by the processor, cause the system to access the previously stored intra-oral image of the patient by accessing the previously stored intra-oral image of the patient from the second memory unit and cause the system to store the new intra-oral image to the non-transitory memory by storing the new intra-oral image to the second memory unit.

15. A method of aiding alignment of a manually positionable intra-oral image capture device, the method comprising:
receiving live image data of a patient from the intra-oral image capture device,
displaying the live image data on a display,
accessing a previously stored intra-oral image of the patient from a non-transitory memory,
automatically generating, by a computer system, an alignment mask based on the accessed previously stored intra-oral image,
displaying the alignment mask on the display overlaid on the live image data,
capturing a new intra-oral image of the patient from the live image data, and
storing the new intra-oral image to the non-transitory memory.

16. The method of claim 15, further comprising determining whether the live image data is aligned with the alignment mask.

17. The method of claim 16, further comprising displaying visual feedback on the display in response to determining that the live image data is aligned with the alignment mask.

18. The method of claim 16, further comprising automatically capturing the new intra-oral image of the patient from the live image data in response to determining that the live image data is aligned with the alignment mask.

19. The method of claim 15, further comprising:
receiving a user input, and
capturing the new intra-oral image from the live image data in response to receiving the user input.

20. The method of claim 15, further comprising generating a first outline of at least a portion of a tooth in the accessed previously stored intra-oral image of the patient by applying an edge-finding routine.

21. The method of claim 20, wherein generating the alignment mask based on the accessed previously stored intra-oral image includes generating the alignment mask based on the first outline.

22. The method of claim 20, further comprising:
determining whether the live image data is aligned with the alignment mask,
displaying the alignment mask on the display in a first color when the system determines that the live data is not aligned with the alignment mask, and
displaying the alignment mask on the display in a second color when the system determines that the live data is aligned with the alignment mask.

23. The method of claim 22, further comprising applying the edge-finding routine to generate a second outline of at least a portion of a tooth in the live image data, and wherein determining whether the live image data is aligned with the alignment mask includes determining whether the first outline matches the second outline.

24. The method of claim 15, wherein displaying the alignment mask on the display overlaid on the live image data includes displaying a partially transparent version of the accessed previously stored intra-oral image overlaid on the live image data.

25. The method of claim 15, further comprising:
displaying a list of previously stored intra-oral images for the patient,
receiving a selection from a user of a previously stored intra-oral image from the list, and
generating the alignment mask based on the selected previously stored intra-oral image.

26. The method of claim 25, further comprising:
identifying a region of interest within an oral cavity of the patient, and
generating the list of previously stored intra-oral images for the patient, wherein the generated list includes only previously stored intra-oral images that correspond to the identified region of interest.

27. The method of claim 15, wherein displaying the live image data on the display includes displaying a real-time feed of images captured by the intra-oral image capture device as a position and orientation of the intra-oral image capture device is manually adjusted by a user.

28. An intra-oral imaging system comprising:
a manually positionable hand-held infrared intra-oral image capture device, the intra-oral image capture device configured to project infrared light onto a tooth and capture an image of at least a portion of the tooth illuminated with the projected infrared light;
a display;
a processor; and
a non-transitory memory storing instructions that, when executed by the processor, cause the system to
receive live image data of the patient from the intra-oral image capture device,
display the live image data on the display,
access a previously stored intra-oral image of the patient from the non-transitory memory,
apply an edge-finding routine to generate a first outline of at least a portion of a tooth in the accessed previously stored intra-oral image of the patient,
apply the edge-finding routine to generate a second outline of at least a portion of a tooth in the live image data,
determine whether the first outline matches the second outline,
display an alignment mask on the display overlaid on the live image data, the alignment mask including the outline of the at least a portion of the tooth in the accessed previously stored intra-oral image of the patient, and
provide a visual indication on the display when the system determines that the first outline matches the second outline.

29. The intra-oral imaging system of claim 28, wherein the instructions, when executed by the processor, cause the system to provide a visual indication on the display when the system determines that the first outline matches the second outline by
displaying the alignment mask on the display in a first color when the system determines that the first outline does not match the second outline, and
displaying the alignment mask on the display in a second color when the system determines that the first outline matches the second outline.

30. The intra-oral imaging system of claim 28, wherein the instructions, when executed by the processor, further cause the system to capture a new intra-oral image from the live image data automatically when the system determines that the first outline matches the second outline.

31. The intra-oral imaging system of claim 28, wherein the instructions, when executed by the process, further cause the system to
receive a user input, and
capture a new intra-oral image from the live image data in response to receiving the user input.

32. The intra-oral imaging system of claim 28, wherein the non-transitory memory further includes a first memory unit and a second memory unit, wherein the instructions are stored on the first memory unit, and wherein the instructions, when executed by the processor, cause the system to access the previously stored intra-oral image of the patient by accessing the previously stored intra-oral image of the patient from the second memory unit.

33. An intra-oral imaging system comprising:
a manually positionable intra-oral image capture device;
a display; and
a processor coupled to the intra-oral image capture device and the display;
wherein the processor is configured to cause the system to
receive live image data of a patient from the intra-oral image capture device,
display the live image data on the display,
access a previously stored intra-oral image of the patient from the non-transitory memory,
apply an edge-finding routine to generate a first outline of at least a portion of a tooth in the previously stored intra-oral image of the patient,
generate an alignment mask based on the first outline,
display the alignment mask on the display overlaid on the live image data,
capture a new intra-oral image of the patient from the live image data, and store the new intra-oral image to the non-transitory memory, display the new intra-oral image on the display, or both.

34. A method of aiding alignment of a manually positionable intra-oral image capture device, the method comprising:
receiving live image data of a patient from the intra-oral image capture device,
displaying the live image data on a display,
accessing a previously stored intra-oral image of the patient from a non-transitory memory,
generating a first outline of at least a portion of a tooth in the previously stored intra-oral image of the patient by applying an edge-finding routine,
generating an alignment mask based on the first outline,
displaying the alignment mask on the display overlaid on the live image data,
capturing a new intra-oral image of the patient from the live image data, and
either storing the new intra-oral image to the non-transitory memory, displaying the new intra-oral image on the display, or both.

\* \* \* \* \*